US006951642B2

United States Patent
Scholz et al.

(10) Patent No.: US 6,951,642 B2
(45) Date of Patent: Oct. 4, 2005

(54) WATER-IN-OIL EMULSIONS WITH ANIONIC GROUPS, COMPOSITIONS, AND METHODS

(75) Inventors: Matthew T. Scholz, Woodbury, MN (US); Gilbert L. Eian, Mahtomedi, MN (US); Ling Lu, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/967,578

(22) Filed: Sep. 28, 2001

(65) Prior Publication Data

US 2003/0118629 A1 Jun. 26, 2003

(51) Int. Cl.⁷ .......................... A61K 31/174; A61K 7/00
(52) U.S. Cl. .................... 424/78.17; 424/401; 514/844; 514/845; 514/846; 514/847; 514/848; 514/938; 514/772.1; 528/801
(58) Field of Search ............................ 424/401, 70.16; 514/844–848, 938; 528/801

(56) References Cited

U.S. PATENT DOCUMENTS

| | | | | |
|---|---|---|---|---|
| 4,147,681 A | * | 4/1979 | Lim et al. .................... | 524/813 |
| 4,172,122 A | | 10/1979 | Kubik et al. | |
| 4,552,685 A | | 11/1985 | Kernstock et al. | |
| 4,552,755 A | | 11/1985 | Randen | |
| 4,816,256 A | | 3/1989 | Randen | |
| 4,847,078 A | * | 7/1989 | Sheppard et al. ........ | 424/78.25 |
| 4,940,579 A | | 7/1990 | Randen | |
| 5,075,400 A | | 12/1991 | Andrade et al. | |
| 5,296,573 A | | 3/1994 | Esselborn et al. | |
| 5,318,995 A | | 6/1994 | Mondet et al. ............. | 514/772 |
| 5,389,676 A | | 2/1995 | Michaels | |
| 5,733,570 A | | 3/1998 | Chen et al. | |
| 5,853,750 A | | 12/1998 | Dietz et al. ................. | 424/448 |
| 5,935,589 A | | 8/1999 | Mukherjee et al. | |
| 5,951,993 A | | 9/1999 | Scholz et al. | |
| 6,086,911 A | | 7/2000 | Godbey | |
| 6,200,596 B1 | | 3/2001 | Swartzmiller et al. | |
| 6,228,354 B1 | | 5/2001 | Jeng ............................. | 424/78 |
| 6,495,158 B1 | * | 12/2002 | Buseman et al. ........... | 424/443 |
| 6,645,476 B1 | | 11/2003 | Morschhäuser et al. | |
| 2001/0029247 A1 | | 10/2001 | Boures et al. | |
| 2003/0064046 A1 | | 4/2003 | Omura et al. | |

FOREIGN PATENT DOCUMENTS

| | | | |
|---|---|---|---|
| EP | 0 011 806 B1 | 6/1980 | |
| EP | 0 446 636 A2 | 9/1991 | |
| EP | 0 522 756 A1 | 1/1993 | ............ A61K/7/48 |
| EP | 0 661 964 B1 | 7/1995 | |
| EP | 0 761 095 A2 | 3/1997 | .......... A01N/52/12 |
| EP | 0 913 445 A1 | 5/1999 | .......... C09J/133/26 |
| EP | 1069142 | 1/2001 | |
| EP | 1 069 142 A1 | 1/2001 | |
| WO | WO 96/03164 A1 | 2/1996 | |
| WO | WO 97/45101 A1 | 12/1997 | |
| WO | WO 97/45101 | 12/1997 | ............ A61K/7/50 |
| WO | WO 02/43689 A2 | 6/2002 | |

OTHER PUBLICATIONS

ICI Companies Datasheet, "ICI Surfactants Arlacel® P135 Polymeric Emulsifier," 1 page total (published prior to Sep. 28, 2001).
Billmeyer, Jr., *Textbook of Polymer Science, Second Edition*, Wiley–Interscience, New York, NY; title page, publication page, and pp. 84–85 (1971).
Cádenas–Valera et al., "Graft copolymers as stabilizers for oil–in–water emulsions Part 1. Synthesis of the copolymers and their behavious as monolayers spread at the air–water and oil–water interfaces," *Colloids and Surfaces A: Physicochemical and Engineering Aspects*, 96:53–67 (1995).
Cádenas–Valera et al., "Graft copolymers as stabilizers for oil–in–water emulsions Part 2. Preparation of the emulsions and the factors affecting their stability," *Colloids and Surfaces A: Physicochemical and Engineering Aspects*, 97:1–12 (1995).
ICI Companies Product Brochure, "Arlacel® P135 Polymeric Emulsifier," Wilmington, DE; 7 pages (Aug., 1997).
Satas, ed., *Handbook of Pressure Sensitive Adhesive Technology 2ⁿᵈ Edition*, Van Nostrand Reinhold, New York, NY; title page, publication page, and p. 172 (1989).
Weast, ed., *CRC Handbook of Chemistry and Physics, 56ᵗʰ Edition*, CRC Press, Cleveland, OH; title page, publication page, preface, and p. D–150 (1975).
Wenninger et al., eds., *The International Cosmetic Ingredient Dictionary and Handbook, 7ᵗʰ Edition*, vols. 1–3, The Cosmetic, Toiletry, and Fragrance Association, Washington, DC; title page, publication page, and table of contents (1997).
Zushun et al., "The Inverse Emulsion Polymerization of Acrylamide Using Poly(Methyl Methacrylate)–Graft–Polyoxyethylene as the Stabilizer," *Journal of Applied Polymer Science*, 79:528–534 (2001).
U.S. Appl. No. 09/966,511, filed Sep. 28, 2001, Mosbey et al.
U.S. Appl. No. 10/052,032, filed Jan. 16, 2002, Lucast et al.
U.S. Appl. No. 10/052,158, filed Jan. 16, 2002, Wang et al.

* cited by examiner

*Primary Examiner*—Sreeni Padmanabhan
*Assistant Examiner*—Gina Yu
(74) *Attorney, Agent, or Firm*—Nancy M. Lambert

(57) ABSTRACT

Water-in-oil emulsions, compositions, and methods that include a vinyl polymer having a pKa of less than 4 that includes anionic group-containing side chains and alkyl-Y-containing side chains, wherein Y is O or NR, wherein R is hydrogen or methyl, and wherein the alkyl group of the alkyl-Y-containing side chain has at least 4 carbon atoms on average in a cyclic, branched-, or straight-chain configuration and optionally including one or more heteroatoms.

20 Claims, No Drawings

WATER-IN-OIL EMULSIONS WITH ANIONIC GROUPS, COMPOSITIONS, AND METHODS

TECHNICAL FIELD

This invention relates to water-in-oil emulsions, compositions containing such emulsions, and methods. The emulsions can be used in moisturizing compositions (e.g., moisturizing skin treatments) to which medical adhesives will adhere, in tissue antiseptic preparations, in personal care compositions such as cosmetics, and in drug delivery compositions, for example. Such emulsions are preferably stable and substantive to mammalian tissue, typically skin.

BACKGROUND

Most of the moisturizing lotions and ointments commonly used to treat and protect mammalian skin consist of oil-in-water emulsions and creams, water-in-oil emulsions and, to a lesser degree, simply oil-based formulations. The oils used are selected from a large group of, cosmetically accepted oils, which are generally recognized by the cosmetic industry for use on skin. Preferred oils have emollient properties. As a whole, these products either do not allow or do not enhance the ability of adhesive products, such as medical tapes, to adhere to skin to which they have been applied.

It is known that certain oil-soluble acrylate polymers, alone or in combination with conventional moisturizing oils, in oil-in-water or water-in-oil emulsions, provide skin treatments. For example oil-soluble acrylate polymers have been used in sunscreening compositions of the water-in-oil type to reduce removal of the sunscreening agent from the skin by swimming or perspiration; in skin moisturizing compositions; with medicaments for topical application to the skin; in mosquito repellent compositions; and in cosmetic compositions such as lip rouges, mascaras, and eyeliners. Such skin treatments that are substantive (i.e., they are not readily removed by simple abrasion or water assault) are particularly desirable.

Water-in-oil emulsion compositions for skin treatment containing low molecular weight oil-soluble acrylate copolymers as emulsifying agents are disclosed in U.S. Pat. No. 4,552,755 (Randen et al.) and U.S. Pat. No. 6,200,596 (Swartzmiller). When these oil-soluble acrylate polymers are used with emollient oils in oil-in-water or water-in-oil emulsions, the result is a skin treatment that provides long lasting skin moisturizing effects. Also, unexpectedly, these compositions enhance (or do not significantly inhibit) the ability of pressure sensitive adhesives to adhere to treated skin. These polymers are prepared from carboxylic acid functional monomers such as acrylic acid, which until the present invention were believed to be important for adhesion of pressure sensitive adhesives. Such products are considered to have high substantivity on tissue.

U.S. Pat. No. 4,172,122 (Kubik et al.) teaches that carboxylic acid functional monomers such as acrylic acid are important in preparing acrylate polymers that can be used in products such as sunscreening products to reduce removal of the sunscreening agent from the skin by swimming or perspiration. Such products are considered to have high substantivity on tissue.

It has also been the conventional belief that carboxylic acid functional monomers, such as acrylic acid, were important for preparing stable water-in-oil emulsions. However, it has been found that the carboxylic acid functional polymers are not typically capable of stabilizing water-in-oil emulsions at low pH, e.g., pH of less than about 5 and especially less than about 4.5. Thus, there is a need for water-in-oil emulsions that are preferably stable over a broad range of pH (e.g., about 3 to about 12).

SUMMARY OF THE INVENTION

According to the present invention, there is provided a water-in-oil emulsion, preferably a stable water-in-oil emulsion. The water-in-oil emulsion includes a vinyl polymer, an oil phase, and a water phase. The vinyl polymer preferably provides moisturizing properties, substantivity, and adhesion enhancement (or adhesion non-inhibiting) treatments for mammalian (preferably, human) tissue (typically skin, as well as other tissues such as mucosal tissue and hair).

In one embodiment, the invention provides a water-in-oil emulsion that includes: a vinyl polymer derived from monomers having a pKa of less than 4 that includes anionic group-containing side chains and alkyl-Y-containing side chains, wherein Y is O or NR, wherein R is hydrogen or methyl, and wherein the alkyl group of the alkyl-Y-containing side chain has at least 4 carbon atoms on average in a cyclic, branched-, or straight-chain configuration and optionally includes one or more heteroatoms; an oil phase; and a water phase. Preferably, the vinyl polymer includes anionic group-containing side chains and alkoxy-containing side chains wherein the alkyl group of alkoxy-containing side chain has 4 to 50 carbon atoms on average in a cyclic, branched-, or straight-chain configuration and optionally includes one or more hereroatoms.

Preferably, the anionic group-containing side chains include groups selected from the group consisting of $(SO_3)_xM$, $(SO_4)_xM$, $(PO_3)_xM$, $(PO_4)_xM$, and combinations thereof, wherein x is 1 or 2 and M is selected from the group consisting of Na, K, Li, Ca, Mg, Zn, a protonated primary amine, a protonated secondary amine, a protonated tertiary amine, a quaternary amine, and combinations thereof. More preferably, the anionic group-containing side chains include sulfate groups ($(SO_4)_xM$), sulfonate groups ($(SO_3)_xM$), phosphate groups ($(PO_4)_xM$), phosphonate groups ($(PO_3)_xM$), and combinations thereof.

More preferably, the vinyl polymer is the reaction product of monomers including: at least one monoethylenically unsaturated alkyl (meth)acrylic monomer having the formula:

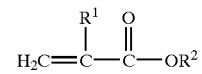

wherein: $R^1$ is hydrogen or methyl; and $R^2$ is a linear, branched, or cyclic alkyl group optionally including one or more heteroatoms; and at least one low pKa acid-containing monomer, or salt thereof, having the formula:

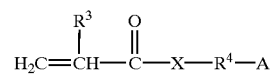

wherein: X is O or $NR^5$; $R^3$ and $R^5$ are each independently hydrogen or methyl; $R^4$ is a linear, branched, or cyclic alkylene, arylene, or aralkylene group optionally including one or more heteroatoms; A is $(SO_3)_xM$, $(SO_4)_xM$, $(PO_3)_xM$, or $(PO_4)_xM$; x is 1 or 2; and M is selected from the group consisting of H, Na, K, Li, Ca, Mg, Zn, a protonated primary amine, a protonated secondary amine, a protonated tertiary amine, a quaternary amine, and combinations thereof.

Preferably, for the monomers, M is hydrogen.

Preferably, about 60 percent by weight (wt-%) to about 95 wt-% of at least one monoethylenically unsaturated alkyl (meth)acrylic monomer and about 5 wt-% to about 40 wt-% of at least one low pKa acid-containing monomer, or salt thereof, are used to prepare the vinyl polymer.

The present invention also provides moisturizing compositions, tissue antiseptic compositions (i.e., tissue disinfectants), personal care compositions, and transdermal drug delivery compositions that include one or more of the water-in-oil emulsions of the present invention. The tissue antiseptic compositions further include one or more antimicrobial agents and the transdermal drug delivery compositions further include one or more pharmaceutical agents.

The present invention also provides methods of using such compositions. These include, methods of moisturizing mammalian skin, methods of disinfecting mammalian tissue (e.g., skin or mucosal tissue), and methods of delivering a pharmaceutical agent to a mammal.

As used herein:

"water-in-oil emulsion" refers to a water-in-oil mixture in which the oil forms a continuous phase and the water is in discontinuous droplets. A water-in-oil emulsion can be distinguished from an oil-in-water emulsion by using an electrical emulsion tester according to the method described in the Examples Section. An oil-in-water emulsion will conduct electricity with relatively low resistance since water forms its external or continuous phase, whereas a water-in-oil emulsion will not conduct, or very poorly conduct, electricity;

"stable" as it relates to an emulsion means that the emulsion will have no visible water separation following one (preferably, two, and more preferably, three) freeze/thaw/centrifuging cycles according to the Emulsion Stability Test Protocol as described in the Examples Section;

"oil phase" in a water-in-oil emulsion refers to all components in the formulation that individually exceed their solubility limit in the water phase; these are materials that generally have solubilities of less than 1% in distilled water, however, water phase components such as salts may decrease the solubility of certain oils resulting in their partitioning into the oil phase;

"water phase" in a water-in-oil emulsion refers to the water present and any components that are water soluble, i.e., have not exceeded their solubility limit in water;

"substantivity" as it relates to an emulsion means that the emulsion can generally resist removal from mammalian tissue (typically skin) by water or abrasion, preferably, a substantive emulsion imparts barrier properties (i.e., resists contamination from external liquids) to mammalian tissue (typically skin);

"pressure sensitive adhesive" or "PSA" refers to a viscoelastic material that displays aggressive tackiness and adheres well to a wide variety of substrates after applying only light pressure (e.g., finger pressure). One well-known means of identifying pressure sensitive adhesives is the Dahlquist criterion. This criterion defines a pressure sensitive adhesive as an adhesive having a 1 second creep compliance of greater than $1 \times 10^{-6}$ square centimeters per dyne ($cm^2$/dyne) as described in *Handbook of Pressure Sensitive Adhesive Technology*, Donatas Satas (Ed.), $2^{nd}$ Edition, p. 172, Van Nostrand Reinhold, New York, N.Y., 1989;

"(meth)acrylate monomers" are acrylic acid esters or methacrylic acid esters of alcohols;

"poly(alkylene oxide) monomers" are used interchangeably herein with poly(alkylene glycol) monomers and refer to ethylenically unsaturated poly(alkylene oxides);

"polymer" includes homopolymers and copolymers of any length; and

"copolymer" includes a polymer of any length (including oligomers) of two or more types of polymerizable monomers, and therefore includes terpolymers, tetrapolymers, etc., which can include random copolymers, block copolymers, or sequential copolymers.

DETAILED DESCRIPTION OF PREFERRED EMBODIMENTS OF THE INVENTION

Emulsions of the present invention include a vinyl polymer (i.e., a polymer derived from vinyl-containing monomers, typically monoethylenically unsaturated monomers) with anionic group-containing side chains and alkyl-Y-containing side chains, wherein Y is O or NR and R is hydrogen or methyl, and wherein the polymer (and preferably, monomers used to from the side chains) has a pKa of less than 4, preferably less than 3; an oil phase; and a water phase. The alkyl-Y-containing side chain can be an alkyl-O group (i.e., an alkoxy moiety) or an alkyl-NR group (i.e., and alkylamino moiety) wherein R is hydrogen or methyl. Preferably, the alkyl groups of the alkyl-Y-containing side chains have at least 4 carbon atoms (on average) in cyclic, branched-, or straight-chain configuration, optionally substituted in or on the chain by heteroatoms (e.g., N, O, or S). As used herein, a "side chain" or "branch" relative to a "backbone" or "main chain" is a group of two or more atoms that branch off from the straight chain of carbon atoms formed by the vinyl polymerization. If desired, the anionic groups and alkyl-Y-containing groups can be in the same side chains.

Preferably, the groups of the anionic group-containing side chains are selected from the group consisting of $(SO_3)_xM$, $(SO_4)_xM$, $(PO_3)_xM$, $(PO_4)_xM$, and combinations thereof, wherein x is 1 or 2 and M is selected from the group consisting of Na, K, Li, Ca, Mg, Zn, a protonated primary amine, a protonated secondary amine, a protonated tertiary amine, a quaternary amine, and combinations thereof. One of skill in the art will understand that for monovalent cations (e.g., Na, K, Li), x is 1, and for divalent cations (e.g., Ca, Mg, Zn), x is 2. More preferably, the anionic group-containing side chains include sulfate groups ($(SO_4)_xM$), sulfonate groups ($(SO_3)_xM$), phosphate groups ($(PO_4)_xM$), phosphonate groups ($(PO_3)_xM$), and combinations thereof.

Such emulsions are surprisingly stable as a result of the anionic group-containing side chains in the vinyl polymer. With certain additives, such as iodine and iodophors, it is highly desirable to formulate an emulsion having a low pH, e.g., below about a pH of 5 and preferably below pH 4.2. To avoid irritation the pH is preferably greater than about 3. As previously discussed, there have been past reports of certain water-in-oil emulsions that contain polymers having carboxylic acid groups to stabilize the emulsions. It has been discovered that these carboxylic acid containing polymers are not capable of stabilizing emulsions typical of the prior art at low pH values. Surprisingly, however, the low pKa (i.e., having a pKa of less than 4) anionic group-containing polymers of the present invention produce very stable emulsions at pH values less than about 5 and even as low as about 3. While not being bound by theory, it is believed that emulsion stabilization in prior compositions, such as those disclosed in U.S. Pat. No. 4,552,755 (Randen et al.), is only achieved at elevated pH where the carboxylic acid groups are ionized. Typically, these polymers having carboxylic acid groups have a pKa value of about 4 to about 4.5, and thus at a pH of 4 most of the carboxylic acid groups would be protonated and incapable of contributing to stability, thereby resulting in unstable water-in-oil emulsions. For example, the pKa (dissociation constant) of acrylic acid is 4.25 (CRC Handbook of Chemistry and Physics, 56$^{th}$ Ed. p. D-150).

The vinyl polymers of the present invention include, for example, polymers derived from vinyl monomers such as (meth)acrylates, (meth)acrylamides, vinyl ether, vinyl acetate, styrene, N-vinyl lactam, N-vinyl pyrrolidone, and N-vinyl caprolactam. Suitable vinyl polymers are soluble (i.e., form transparent homogenous solutions) or dispersible in the oil phase and tend to be insoluble or sparingly soluble in the water phase. Preferred vinyl polymers are soluble in the oil phase. More preferred vinyl polymers are acrylate polymers derived from one or more types of monoethylenically unsaturated (meth)acrylic monomers and one or more types of monoethylenically unsaturated low pKa acidic (i.e., acid-containing) (meth)acrylic monomers or salts thereof.

A preferred class of acrylate polymers useful in the stable water-in-oil emulsions of the invention include polymers derived from the polymerization of at least one monoethylenically unsaturated alkyl (meth)acrylic monomer, preferably an alkyl (meth)acrylic acid ester (i.e., an alkyl acrylate or alkyl methacrylate), wherein the alkyl group has at least 4 carbon atoms (on average) and no greater than 22 carbon atoms (on average), and at least one monoethylenically unsaturated low pKa acid-containing monomer, preferably, a monoethylenically unsaturated sulfonic acid (meth)acrylic acid ester monomer. Depending on the properties of the resultant polymer, the monoethylenically unsaturated (meth) acrylic acid esters used to prepare the polymer can have just short alkyl groups (e.g., at least 4 carbon atoms (on average) and no greater than 14 carbon atoms (on average)), or just long alkyl groups (e.g., at least 15 carbon atoms (on average) and no greater than 22 carbon atoms (on average)), or mixtures of monoethylenic ally unsaturated (meth)acrylic acid esters with short alkyl groups can be used in combination with monoethylenically unsaturated (meth)acrylic acid esters with long alkyl groups.

It should be noted that the polymers of the present invention prepared from low pKa acid-containing monomers when formulated into compositions having pH values of 2–12 and certainly from 3–12 will be anionic due to ionization of the low pKa acidic groups. It should also be noted that the polymers of the present invention may optionally be prepared from carboxylic acid-containing monomers in addition to the low pKa acid-containing monomers.

Alkyl (Meth)acrylic Monomers

One preferred class of vinyl polymers used in the emulsions of the present invention contains at least one copolymerized monoethylenically unsaturated alkyl (meth)acrylic monomer. As used herein, the "monoethylenically unsaturated" term in the alkyl (meth)acrylic monomer refers to the acrylic unsaturation. Preferably, "alkyl (meth)acrylic" monomers include (meth)acrylamides (e.g., octylacrylamide), (meth)acrylates, and combinations thereof. More preferably, the alkyl (meth)acrylic monomer is an alkyl (meth)acrylic acid ester (i.e., an alkyl acrylate or alkyl methacrylate), wherein the alkyl group has at least 4 carbon atoms (on average). Preferably, the alkyl group has no greater than 50 carbon atoms, more preferably, no greater than 36 carbon atoms, and most preferably, no greater than 22 carbon atoms (on average). Alternatively stated, these (meth)acrylate monomers are (meth)acrylic acid esters of alkyl alcohols (preferably, nontertiary alkyl alcohols), the alkyl groups of which preferably include, 4 to 22 carbon atoms (on average). Of these, one preferred alkyl group includes 4 to 14 carbon atoms, and more preferably 6 to 8 carbon atoms (on average). Another preferred alkyl group includes 14 to 22 and more preferably 18 to 20 carbon atoms (on average). The alkyl group can optionally contain heteroatoms and can be linear, branched, or cyclic.

Preferred alkyl (meth)acrylate monomers have the following general Formula (I):

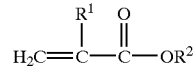

Formula (I)

wherein $R^1$ is hydrogen or methyl, the latter corresponding to where the (meth)acrylate monomer is a methacrylate monomer, and $R^2$ is broadly selected from linear, branched, or cyclic alkyl groups and optionally includes one or more heteroatoms (e.g., N, O, or S). The number of carbon atoms in the $R^2$ group is as outlined above for the alkyl group of the alkyl-Y group (e.g., alkoxy group).

Examples of suitable (meth)acrylate monomers having shorter alkyl groups useful in the present invention include, but are not limited to, n-butyl acrylate, decyl acrylate, 2-ethylhexyl acrylate, hexyl acrylate, isoamyl acrylate, isodecyl acrylate, isononyl acrylate, isooctyl acrylate, lauryl acrylate, 2-methylbutyl acrylate, 4-methyl-2-pentyl acrylate, ethoxy ethoxyethyl acrylate, isobornyl acrylate, and the like. Particularly preferred of these are n-butyl acrylate, 2-ethylhexyl acrylate, isooctyl acrylate, lauryl acrylate, and mixtures thereof.

Examples of suitable (meth)acrylate monomers having longer alkyl groups useful in the present invention include, but are not limited to, stearyl acrylate, stearyl methacrylate, behenyl acrylate, acrylate esters of $C_{14}$–$C_{32}$ Gerbet alcohols, and the like. Particularly preferred of these is stearyl methacrylate. Various combinations of monoethylenically unsaturated (meth)acrylate monomers can be used in the emulsions of the present invention.

Preferably, the monoethylenically unsaturated alkyl (meth)acrylic monomer(s) can be used in an amount of at least about 60 weight percent (60 wt-%), and more preferably, at least about 75 wt-%, based on the total weight of the polymerizable composition. Preferably, the monoethylenically unsaturated alkyl (meth)acrylic monomer(s) can be used in an amount of no greater than about 95 wt-%, and more preferably, no greater than about 90 wt-%, based on the total weight of the polymerizable composition.

Low pKa Monomers

One or more monoethylenically unsaturated acid-containing monomers, or salts thereof (i.e., anionic group-containing monomers), having a pKa of less than 4, preferably less than 3 (as measured on the unpolymerized monomer), can be copolymerized with the alkyl (meth) acrylic monomer(s). These monomers are selected for use in the emulsions such that they improve emulsion stability.

Preferably, the acid-containing monomers, or salts thereof, include groups such as $(SO_3)_xM$, $(SO_4)_xM$, $(PO_3)_xM$, $(PO_4)_xM$, and combinations thereof, wherein x is 1 or 2 and M selected from the group consisting of H, Na, K, Li, Ca, Mg, Zn, a protonated primary amine, a protonated secondary amine, a protonated tertiary amine, a quaternary amine, and combinations thereof. Preferably, M is H. One of skill in the art will understand that for monovalent cations (e.g., H, Na, K, Li), x is 1, and for divalent cations (e.g., Ca, Mg, Zn), x is 2.

It is presently preferred to synthesize the vinyl polymer from low pKa acid-containing monomers in their acid (i.e., protonated) form, rather than their salt (i.e., anionic) form.

Therefore, preferably, M is H. In use in the emulsions of the present invention, however, these groups will be ionized at pH values above 2 and especially above 3.

Preferred low pKa acid-containing monomers, or salts thereof, are (meth)acrylic monomers and preferably have the following Formula (II):

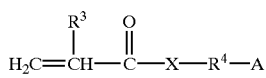

Formula (II)

wherein: X is O or $NR^5$; $R^3$ and $R^5$ are each independently hydrogen or methyl; $R^4$ is a linear, branched, or cyclic alkylene, arylene, or aralkylene group optionally including one or more heteroatoms (e.g., N, O, and S); and A is $(SO_3)_xM$, $(SO_4)_xM$, $(PO_3)_xM$, $(PO_4)_xM$, wherein x is 1 or 2.

The M group may be monovalent ions selected from H, Na, K, and Li when x is 1. The M group may also be divalent ions selected from Ca, Mg, and Zn provided that the appropriate ionic stoichiometry is preserved (i.e., x is 2). M may also be selected from protonated primary, secondary, and tertiary amines as well as quaternary amines, such as tetramethylamine, triethanolammonium, diethanolammonium, 2-ammonium-2-methyl-1,3-propanediol, and stearyl ammonium, and the like, when x is 1. Preferably, M is H.

More preferably, the acid-containing monomers, or salts thereof, include sulfate groups (($SO_4)_xM$ wherein M≠H), sulfonate groups (($SO_3)_xM$ wherein M≠H), sulfonic acid ($SO_3H$), sulfuric acid monoester groups ($SO_4H$), phosphate groups (($PO_4)_xM$ wherein M≠H), phosphonate groups (($PO_3)_xM$ wherein M≠H), phosphonic acid groups ($PO_3H$), phosphoric groups monoester ($PO_4H$), and combinations thereof. Most preferably, for the starting monomers, M is H (i.e., the monomers are in their protonated form). It will be understood, that the resultant polymer, which primarily includes anionic groups (i.e., salts), there can also be small amounts of acidic (i.e., protonated) groups.

It will be understood by one of skill in the art that the $SO_4$ and $PO_4$ groups will be bonded to $R^4$ through an oxygen, whereas the $SO_3$ and $PO_3$ groups will be bonded to $R^4$ through the sulfur or phosphorus, respectively. The $R^4$ group preferably includes at least 2 carbons, more preferably, at least 3 carbons, and most preferably, at least 4 carbons, on average. The $R^4$ group preferably includes no more than 18 carbons, more preferably, no more than 14 carbons, and most preferably, no more than 12 carbons, on average.

Preferably, the low pKa monomer(s) can be used in an amount of at least about 5 wt-%, preferably at least about 8 wt-%, and more preferably at least about 10 wt-%, based on the total weight of the polymerizable composition. Preferably, the low pKa monomer(s) can be used in an amount of no more than about 40 wt-%, based on the total weight of the polymerizable composition.

Optional Poly(alkylene oxide) Monomers

One or more monoethylenically unsaturated poly (alkylene oxide) monomers can be copolymerized with the alkyl (meth)acrylic monomer(s) and low pKa monomer(s). The monoethylenically unsaturated poly(alkylene oxide) monomers are selected for use in the emulsions such that they improve emulsion stability. Preferred monoethylenically unsaturated poly(alkylene oxide) monomers are mono-ethylenically unsaturated poly(alkylene oxide) (meth) acrylic monomers.

Particularly preferred monoethylenically unsaturated poly (alkylene oxide) monomers have the following general Formula (III):

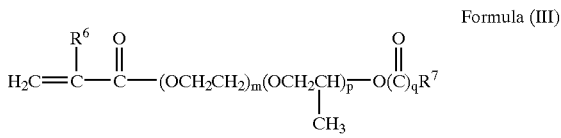

Formula (III)

wherein: m is at least 2; p is 0 to 50; q is 0 or 1; $R^6$ is hydrogen or methyl, and $R^7$ is hydrogen or linear or branched alkyl and/or aryl groups. In this representation, the isopropylene oxide groups (the "p" groups) and the ethylene oxide groups (the "m" groups) can be arranged in a reversed, alternating, random, or block configuration. In any one monomer, m is preferably at least about 4. Preferably, m is no greater than about 115, more preferably, no greater than about 45, and most preferably, no greater than about 25. Preferably, p is 0. Preferably, q is 0. The $R^7$ group preferably includes at least 1 carbon atom, on average. The $R^7$ group preferably includes no more than 50 carbons, on average, more preferably, no more than 22 carbons, on average, and most preferably, is methyl.

Preferably, the monoethylenically unsaturated poly (alkylene oxide) monomers are poly(ethylene oxide) monomers or poly(ethylene oxide/propylene oxide) monomers. A particularly preferred such monomer is poly(ethylene oxide) monomer. The poly(ethylene oxide/propylene oxide) monomers can be random, sequential, or block. Examples of useful monoethylenically unsaturated poly(alkylene oxide) monomers include, but are not limited to, acrylate-terminated poly(ethylene oxide), methacrylate-terminated poly(ethylene oxide), methoxy poly(ethylene oxide) methacrylate, butoxy poly(ethylene oxide) methacrylate, acrylate-terminated poly(ethylene glycol), methacrylate-terminated poly(ethylene glycol), poly(ethylene oxide) diacrylate, poly(ethylene oxide) dimethacrylate, and combinations thereof.

Suitable poly(alkylene oxide) monomers include acrylate and methacrylate esters prepared from mono-hydroxyl-terminated poly(lower alkylene oxides) such as polyethylene and polypropylene glycols commercially available under the trade designation CARBOWAX from Union Carbide Corp. in a variety of molecular weights (e.g., CARBOWAX 350, CARBOWAX 550, CARBOWAX 750, CARBOWAX 2000, and CARBOWAX 5000); and their corresponding alkyloxy-terminated derivatives. Examples of suitable poly(alkylene oxide) monomers include those commercially available under the trade designations CD 550 (methoxy polyethylene glycol (350) monomethacrylate), and CD 552 (methoxy polyethylene glycol (550) monomethacrylate), all of which are available from Sartomer Chemicals, Exton, Pa.; and those commercially available under the trade designations M90G (methoxy polyethylene glycol (about 9 ethyleneoxy units, i.e., groups) monomethacrylate) and M230G (methoxy polyethylene glycol (about 23 ethyleneoxy units) monomethacrylate), all of which are available from Shin-Nakamura Chemicals, Wakayama City, Japan; and those commercially available as poly(ethyleneglycol) methyl ether methacrylate (available with molecular weights of approximately 300, approximately 475, and approximately 1100) from Sigma-Aldrich, St. Louis, Mo. An example of a poly(alkylene oxide) monomer that also includes a long chain alkyl group is behenyl PEG-25 methacrylate commercially available as SIPOMER BEM from Rhodia, Cranbury, N.J. Preferred poly(alkylene oxide) monomers include poly(ethyleneglycol) methyl ether methacrylate (with molecular weights of approximately 300, approximately 475, and approximately 1100). Various combinations of monoethylenically unsaturated poly(alkylene oxide) monomers can be used in the emulsions of the present invention.

Optionally, the monoethylenically unsaturated poly (alkylene oxide)monomer(s) can be used in an amount of at least about 10 wt-%, based on the total weight of the polymerizable composition. Optionally, the monoethylenically unsaturated poly(alkylene oxide) monomer(s) can be used in an amount of no more than about 40 wt-%, based on the total weight of the polymerizable composition.

Preparation of the Vinyl Polymer

The preparation of the vinyl polymers from monomers of the type disclosed herein is well documented in the literature and can be carried out by free radical initiated bulk, solution, precipitation, suspension or emulsion techniques. Generally, the solution technique is preferred. Specific polymerization methods used in this invention are discussed in the Examples Section.

Generally for the solution polymerization technique, the monomers are dissolved in a suitable solvent, a free radical initiator is added, the solution is purged with inert gas (nitrogen) to remove oxygen, and the initiator is activated. The amount of solvent is generally about 30 wt-% to about 80 wt-% based on the total weight of the reactants and solvents. Generally the initiator is present in an amount of about 0.005 part to about 1 part based on 100 parts of total monomer. Activation of the initiator may be by thermal decomposition, radiation induced decomposition, or by chemical reaction via a redox couple. Thermally activated initiators are most preferred.

Usually the solution is agitated during the reaction to mix the components. Optionally, a chain transfer agent may be added to the reaction to regulate the molecular weight of the polymer product. The monomer conversion may vary depending on the viscosity of the reaction solution and the reaction temperature. Typically, monomer conversion of 98 percent or greater is obtained within 48 hours. Suitable solvents for the polymerization reaction may be any organic liquid that is inert to the reactants and product and will not otherwise adversely affect the reaction. Such solvents include alcohols, esters, ketones, aliphatic or aromatic hydrocarbons, and mixtures thereof. The reaction may be done in a relatively low boiling solvent, and after the reaction is complete the product may be exchanged into the higher boiling emollient oil solvent by adding the emollient oil to the reaction mixture and evaporating the lower boiling reaction solvent under reduced pressure. The emollient oils may optionally be used as reaction solvents for the polymerization.

Polymerization Initiators. A free radical initiator is preferably added to aid in the copolymerization of (meth) acrylate and various comonomers. The type of initiator used depends on the polymerization process. Suitable initiators include photoinitiators, thermal initiators, redox initiators, etc. Photoinitiators that are useful for polymerizing the polymerizable mixture of monomers include benzoin ethers such as benzoin methyl ether or benzoin isopropyl ether, substituted benzoin ethers such as 2-methyl-2-hydroxypropiophenone, aromatic sulfonyl chlorides such as 2-naphthalenesulfonyl chloride, and photoactive oxides such as 1-phenyl-1,1-propanedione-2-(O-ethoxycarbonyl) oxime. An example of a commercially available photoinitiator under the trade designation IRGACURE 651 is 2,2-dimethoxy-1,2-diphenylethane-1-one (commercially available from Ciba-Geigy Corp.). Examples of suitable thermal initiators include those available under the trade designations VAZO-64 (2,2'-azobis(isobutyronitrile) and VAZO-67 (2,2'-azobis(2-methylbutanenitrile), both of which are available from DuPont Co., hydroperoxides, such as tert-butyl hydroperoxide, and peroxides, such as benzoyl peroxide and cyclohexane peroxide. Examples of suitable redox initiators, such as tert-butyl hydroperoxide plus a reducing agent (e.g., tertiary amines, ferrous sulfate, sodium formaldehyde sulfoxylate, and sodium bisulfite).

Polymerization Chain Transfer Agents. Optionally, the composition also includes a chain transfer agent to control the molecular weight of the polymerized compositions. Chain transfer agents are materials that regulate free radical polymerization and are generally known in the art. Suitable chain transfer agents include halogenated hydrocarbons such as carbon tetrabromide, and sulfur compounds such as lauryl mercaptan, butyl mercaptan, ethanethiol, isooctylthioglycolate (IOTG), 2-ethylhexyl thioglycolate, 2-ethylhexyl mercaptopropionate, 2-mercaptoimidazole, and 2-mercaptoethyl ether and mixtures thereof. The amount of chain transfer agent that is useful depends upon the desired molecular weight and the type of chain transfer agent. The chain transfer agent is typically used in amounts from about 0.001 part to about 10 parts by weight per 100 parts of total monomer. Alternatively, the solvent (e.g., ethanol, isopropanol) could serve as the chain transfer agent.

Emulsion Formulation and Preparation

The molecular weight of the polymers used in the compositions may vary over a broad range. The molecular weight is preferably suitably large to provide the requisite binding effect between a coating composition containing the emulsion and an adhesive applied over the coating composition. The upper limit is determined largely by formulation requirements. As the molecular weight increases, the polymers tend to become too viscous to formulate easily into cosmetically appealing compositions. Preferably, the vinyl polymers have an inherent viscosity (in units of deciliters per gram (dl/g)) of at least about 0.2, more preferably, at least about 0.4, and preferably, no greater than about 3.0, more preferably, no greater than about 2.0, when measured at 0.30 wt-% of the polymer in tetrahydrofuran.

Preferably, the vinyl polymers have a low pKa acid equivalent weight, calculated in the free acid from of the low pKa acid-containing monomer, of at least about 1000, and more preferably, at least about 1250, and most preferably, at least about 1500, grams of polymer per equivalent of low pKa acid. Preferably, the vinyl polymers have an acid equivalent weight of no greater than about 6500, and more preferably, no greater than about 4000, and most preferably, no greater than about 2500, grams of polymer per equivalent of low pKa acid. In the present invention, a "low pKa" acid is one that has a pKa of less than 4. It should be noted that the polymers of the present invention can be prepared from acids having a higher pKa, such as carboxylic acid-containing monomers, in addition to the low pKa acid-containing monomers.

One or more vinyl polymers are preferably present in an emulsion of the present invention in a total amount of at least about 0.25 wt-%, and more preferably, at least about 0.5 wt-% based on the total weight of the emulsion. One or more vinyl polymers are preferably present in an emulsion of the present invention in a total amount of no more than about 10 wt-% and more preferably, no more than about 3 wt-% based on the total weight of the emulsion.

The oil used in the emulsions of the present invention can be selected from a wide variety of oils or mixtures of oils that are conventionally used in the cosmetic art. Preferably, the oil is an "emollient oil," which as used herein refers to any dermally acceptable oil or mixture of oils which forms a barrier on the skin capable of retarding the evaporation of water from the skin. The oil base of the emulsions can be solid or liquid, but the entire formulation should be somewhat fluid at skin temperatures for ease of application.

Examples of suitable oils include silicone fluids, saturated fatty esters and diesters such as diisopropyl adipate, dicapryl adipate, diisopropyl sebacate, dioctyl sebacate, dioctyl ether, glyceryl tricaprylate/caprate, diethyleneglycol dicaprylate/caprate, propylene glycol dipelargonate, polyalkoxylated alcohols such as 15 mole propoxylate of stearyl alcohol, paraffin oils and waxes, animal and vegetable oils including mink oil, coconut oil and derivatives thereof, palm oil, corn oil, cocoa butter, petrolatum, coconut oil, sesame oil, and the like, lanolin derivatives, fatty alcohols such as isostearyl alcohol, isocetyl alcohol, cetyl/stearyl alcohol, and straight chain alcohols from $C_6$–$C_{18}$ and certain petroleum distillates which are toxicologically safe such as $C_8$–$C_{22}$ isoparaffin hydrocarbon solvents, e.g., isooctane and isododecane. Other oils are water insoluble esters such as short chain esters of long chain alcohols or acids. Examples include methyl behenate, methyl stearate, arachidyl propionate, behenyl lactate, stearyl acetate, isopropyl palmitate, 2 mole propoxylate of myristyl propionate, isopropyl myristate, cetyl palmitate, butyl stearate, and glycerol monoerucate. The oils mentioned in this list are merely examples and are not intended to limit the invention in any way.

Oils that are particularly preferred in the practice of the present invention include isopropyl palmitate, coconut oil, isooctane, isododecane, petrolatum, cetyl palmitate, cetyl/stearyl alcohol, diethyleneglycol dicaprylate/caprate, diisopropyl sebacate, glyceryl tricaprylate/caprate, diiospropyl adipate, dicapryl adipate, silicone fluids, 2 mole propoxylate of myristyl propionate, and 15 mole propoxylate of stearyl alcohol (e.g., that commercially available under the trade designation ARLAMOL E from Uniqema, Wilmington, Del.).

Preferably, one or more oils used in the emulsions of the present invention are present in a total amount of at least about 20 wt-%, more preferably, at least about 30 wt-%, and most preferably, at least about 40 wt-%, based on the total weight of the emulsion. Preferably, one or more oils used in the emulsions of the present invention are present in a total amount of no more than about 80 wt-%, more preferably no more than about 70 wt-%, and most preferably no more than about 60 wt-%, based on the total weight of the emulsion.

The emulsions preferably include at least about 15 wt-% water, more preferably, at least about 30 wt-% water, and most preferably, for certain embodiments, such as for creams and lotions, the emulsions include at least about 40 wt-% water, based on the total weight of the emulsion. They preferably include no more than about 70 wt-% water, and more preferably, no more than about 55 wt-% water, based on the total weight of the emulsion.

The water-in-oil emulsions are generally prepared by heating, independently, the oil phase (containing the vinyl polymer and optional ingredients, e.g., surfactants) and the water phase (containing optional ingredients, e.g., humectants and stabilizers), and slowly adding the water phase to the oil phase with good agitation. Homogenization is preferred, but may not be necessary. Upon cooling, other optional ingredients may be added, e.g., skin barrier/protectant materials, preservatives, and thickeners.

Preferred emulsions of the present invention have substantivity properties when applied to skin and thus are able to resist water and/or abrasive removal and act as a barrier to external liquid challenges, such as from potential skin contaminants such as urine, blood, and feces.

Humectants are also advantageously incorporated into the water phase of the compositions of the present invention. As used herein the term "humectant" refers to polar compounds or mixtures of compounds that act to retain or absorb moisture. As used herein the term "humectant" refers to polar compounds or mixtures of compounds that act to retain or absorb moisture. Suitable humectants include, but are not limited to, polyols, such as glycerin, propylene glycol, dipropylene glycol, polypropylene glycol, glycerine ethoxylates, methyl glucose ethoxylates, polyethylene glycol, polyethylene/polypropylene glycols, and sorbitol. Dipropylene glycol and polypropylene glycol are particularly preferred humectants.

The addition of low levels of stabilizing ingredients in the water phase can also be advantageous. Salts such as magnesium sulfate may be useful emulsion stabilizers, and they do not significantly affect the water resistance of the formulations. However, the addition of magnesium sulfate can, in some instances, inactivate bioactive agents, e.g., antimicrobial agents such as chlorhexidine gluconate. The addition of water-soluble gums such as guar derivatives, xanthan gum, and thickeners such as hydroxy ethyl cellulose, hydroxy propyl cellulose and carboxyl vinyl polymers may be helpful in stabilizing the emulsion. Oil phase emulsion stabilizers include ethylene/acrylic acid copolymer such as an ethylene/acrylic acid copolymer available under the trade designation AC540 from Allied Signal, Morrison, N.J., N-vinyl pyrrolidone/olefin copolymers such as such as that available under the trade designation GANEX V-216 from ISP International Specialty Products, Wayne, N.J.

The addition of silicone oil dimethicone to the oil phase prior to preparation of the emulsion can also be advantageous in improving the ability of the emulsions to act as a barrier to urine, feces, or other indigenous and exogenous materials when used as moisturizing compositions (e.g., moisturizing skin treatments) and other personal care compositions. The dimethicone may be present in concentrations up to about 5 wt-% and preferably are present in concentrations greater than about 1.0 wt-%, based on the total weight of the emulsion.

Auxiliary emulsifiers conventionally used in cosmetic formulations can be employed to ensure stability and extend shelf life of any of the compositions of the present invention. Such auxiliary emulsifiers are distinct from the vinyl polymers described herein, and typically function as surfactants. It has also been found that the auxiliary emulsifier can influence substantivity to some extent. Auxiliary emulsifiers that provide good substantivity include polyalkoxylated glyceryl $C_6$–$C_{22}$ alkyl esters such as 82-mole ethoxylate of glyceryl tallowate, glyceryl $C_6$–$C_{22}$ alkyl esters such as glyceryl stearate, $C_{12}$–$C_{18}$ alkyl carboxylic acids such as stearic acid, $C_{12}$–$C_{22}$ polyalkoxylates such as laureth-4, polypropylene glycol (PPG) (15) stearyl ether (commercially available under the trade designation ARLAMOL E from Uniqema, Wilmington, Del.), and 20-mole ethoxylate of cetyl/stearyl alcohol, polyetherpolyester polymers such as polyethylene glycol (PEG) (30) polyhydroxy-stearate, MW of approximately 5000 (commercially available under the trade designation ARLACEL P135 from ICI, Wilmington, Del.). The auxiliary emulsifier is preferably present in an amount of at least about 1 wt-%, more preferably, at least about 5 wt-%, and preferably, no more than about 20 wt-%, more preferably, no more than about 10 wt-%, based on the total weight of the emulsion.

Certain emulsions of the present invention find particular utility as moisturizing skin treatments. Preferably, such skin treatments are substantive. They preferably are compatible with antimicrobial agents and do not typically adversely affect adhesion of pressure sensitive adhesive articles, as discussed in greater detail below.

Certain emulsions of the present invention find particular utility as presurgical and precatherization tissue (e.g., skin) antiseptics (i.e., disinfectants) and in general for disinfecting skin and mucosal tissue with an antimicrobial composition, which is preferably substantive. The preferred compositions are not only substantive but allow for immediate placement of adhesive products, such as medical tapes, surgical incise drapes or wound dressings, directly over the coated skin. The emulsions of this invention not only allow adhesion over of these products but in many cases actually enhance the adhesion and may especially enhance the adhesion of these products in moist or wet conditions such as beneath a surgical incise drape exposed to body fluids and around a catheter or other percutaneous puncture.

The emulsions of the present invention are advantageously compatible (i.e., retain biological activity and emulsion stability) with at least one bioactive agent. Bioactive agents typically include antimicrobials such as antibacterials, antivirals, antifungals, as well as corticosteroids such as hydrocortisone, and topical anesthetics.

A preferred bioactive agent is an antimicrobial. Examples of antimicrobial agents include iodine and its complexed forms, which are commonly referred to as iodophors. Iodophors are iodine complexes with polyethylene glycol and its derivatives, N-vinyl caprolactam containing polymers such as polyvinylpyrrolidone, as well as other polymers that tend to hydrogen bond with hydrogen iodide or hydrogen triiodide or complex with salts such as sodium or potassium triiodide. Other antimicrobials include chlorhexidine salts such as chlorhexidine gluconate (CHG); parachlorometaxylenol (PCMX); triclosan; hexachlorophene; fatty acid monoesters of glycerin and propylene glycol such as glycerol monolaurate, glycerol monocaprylate, glycerol monocaprate, propylene glycol monolaurate, propylene glycol monocaprylate, propylene glycol monocaprate; phenols; surfactants and polymers that include a $C_{12}$–$C_{22}$ hydrophobe and a quaternary ammonium group; polyquaternary amines such as polyhexamethylene biguanide; quaternary silanes; hydrogen peroxide; phenols; silver and silver salts such as silver chloride, silver oxide and silver sulfadiazine; and the like. Preferred antimicrobial agents are iodophors since they are capable of ensuring long term antimicrobial efficacy. A particularly preferred iodophor is povidone-iodine and most preferably povidone-iodine USP. Various combinations of antimicrobial agents can be used in the emulsions of the present invention.

If added to an emulsion, one or more antimicrobial agents are preferably present at a level of at least about 0.05 wt-%, and more preferably, at least about 0.25 wt-%, based on the total weight of the emulsion. One or more antimicrobial agents are preferably present at a level of no greater than about 10.0 wt-%, and more preferably, no greater than about 8.0 wt-%, based on the total weight of the emulsion.

It may also be suitable to add systemically active pharmaceutical agents to the water-in-oil emulsions of the present invention to produce transdermal drug delivery vehicles, which are preferably substantive. When applied to the skin the pharmaceutical agent would be transported across the skin into the bloodstream. In this regard it maybe particularly appealing to add penetration enhancing agents particularly to the oil phase, such as lauryl alcohol, oleyl alcohol, lauramide DEA, lauryl pyrrolidone-5-carboxylate, and ascorbyl palmitate. Penetration enhancing agents such as glycerin, propylene glycol, and tetraglycol may also be added to the water phase. Other penetration enhancing agents, as well as exemplary pharmaceutical agents, that may be added to the water-in-oil emulsions of the present invention may be found in U.S. Pat. No. 6,086,911 (Godbey).

When applied to mammalian (preferably, human) skin (or other tissue such as mucosal tissue or hair), the emulsions of the present invention form an oil film on the tissue surface. Surprisingly, in spite of the oiliness and moisturizing effects of the emulsions, pressure sensitive adhesives, such as used on medical tapes, IV site dressings, and surgical incise drapes, adhere at least as well and, in most cases, more strongly to the emulsion-treated tissue (typically, skin) than to untreated tissue (typically, skin). Medical tapes and dressings that adhere particularly well to the emulsions include those utilizing acrylate, block copolymer (e.g. adhesives based on KRATON polymers commercially available from Kraton Polymers, Houston, Tex.), and rubber based pressure sensitive adhesives. Examples are tapes and dressings commercially available from 3M Company under the trade designations TRANSPORE, BLENDERM, STERI-STRIPS, MICROPORE, TEGADERM, STERIDRAPE, and IOBAN II.

A pressure sensitive adhesive article (e.g., tape, incise drape, wound dressing, and the like) applied over the emulsions (or compositions containing the emulsions) of the present invention on mammalian tissue, typically skin (after allowing the emulsion or composition containing the emulsion to dry for at least 15 seconds), preferably adheres at a level of at least about 50% of the level of adhesion of the pressure sensitive adhesive article applied directly to the tissue, typically skin (i.e., without the emulsion). This can be measured by applying a thin uniform amount of the emulsion to skin as described in the Examples Section, applying the adhesive article, and rolling with a 4.5-pound (2.1-kg) 2-inch (5.1-cm) wide roller. After waiting 1–5 minutes the adhesive article is removed at a peel angle of 180 degrees at a speed of 12 inches/minute (30.5 cm/min). Due to the variability in skin types a statistically relevant sample is employed which is typically at least 8 subjects where at least 2 strips are applied to the backs of each subject.

The emulsions of this invention, if applied in a thin film to mammalian tissue, typically skin, preferably allow instantaneous adhesion of medical adhesive products. That is, typically and preferably, within about 60 seconds, and often, in as little as 15 seconds, of application of a thin film, an adhesive product can be applied over the composition that will exhibit good adhesion in as little as about 5 minutes, preferably as little as about 60 seconds, and most preferably in as little as about 40 seconds. In many of the preferred cases the adhesion over the compositions of the present invention will exceed that of the product applied to dry unprepared tissue (typically, skin).

The oil phase used in the water-in-oil emulsions of the present invention are preferably compatible with the medical pressure sensitive adhesives that may be placed over the composition. Not all oils will be compatible (i.e., allow good adhesion of the article) with all adhesives. For polyacrylate-based pressure sensitive adhesives, the oil phase preferably contains an ester-functional emollient oil or other emollient oil that is capable of plasticizing the adhesive, such as those described in U.S. Pat. No. 5,951,993 (Scholz et al.). For example, with most pressure sensitive adhesives that include predominantly alkyl acrylates, such as isooctylacrylate or 2-ethylhexylacrylate, emollient oils such as glyceryl tricaprylate/caprate, diiospropylsebacate, isopropylplamitate, diisopropyl adipate, diethyleneglycoldioctanoate/diiosnonanoate, and the like, are very effective. Also preferred are certain ether-based emollient oils. For example, with most polyacrylate pressure sensitive adhesives that include predominantly isooctylacrylate or 2-ethylhexylacrylate, dimethylisosorbide and PPG2 methyl ether are effective. Preferably, the oil is not too polar. For example, materials such as glycereth 7 diisononanoate and glycerol triacetate may tend to reduce the adhesion of the medical pressure sensitive adhesive significantly. It should be noted, however, that minor amounts of more polar components may be added to the oil phase and still allow good drape adhesion.

Importantly, since the continuous phase of the emulsion is a water-insoluble oil, the adhesion of a medical adhesive product is not easily undercut by water or body fluids. This is particularly important for use of an emulsion as a presurgical tissue antiseptic ("prep"), for use on skin or mucosal tissue (preferably, skin), over which an incise drape is optionally applied. In these surgical applications blood, saline, and other body fluids are constantly present which may tend to wash water-soluble preps away and perhaps even into the wound. The water-in-oil emulsion preps of the present invention, however, resist wash off very well.

Furthermore, the water resistance is also important for preps over which an adhesive product is applied. For example, when using a surgical incise drape (adhesive coated film through which a surgical incision is made) adhesion to the composition throughout the surgery is important. Therefore, resistance to water and body fluid infiltration from the wound edge is important. This is similarly very important for use around percutaneous devices such as a catheter insertion site. These sites often have fluid build up around the catheter, which can affect adhesion. The adhesion of dressings such as thin film adhesive coated dressings over the compositions of the present invention ensures a strong bond despite the presence of moisture.

Another key advantage of the preferred emulsions of the present invention, which is particularly important for tissue antiseptics such as preoperative surgical preps and IV site preps, is that the emulsions may be removed gently with a cloth, gauze or other fabric optionally using a mild detergent for complete removal. No organic solvent-based removers are necessary but may be used if desired.

The emulsions of the present invention may be used to form milks (i.e., low viscosity emulsions similar in consistency to cow's milk), lotions, and creams that are preferably water-repellent, moisturizing, and long lasting compared to most other commercially available skin lotions. These features are important for ostomy or incontinence applications where protection of the skin from irritating body fluids such as urine, feces, and intestinal fluids is desired. The fact that the emulsions may enhance adhesion of pressure sensitive adhesives, allows them to be used to protect skin surrounding stomas, dermal ulcers, diseased skin, or surgical wounds without interfering with the application of adhesive wound dressings. This is also a major advantage over other percutaneous dressings when the present-invention emulsions are used in challenging fluid environments associated with surgical incise drapes, IV site dressings, and other dressings.

The emulsions of the present invention are useful in the preparation of various personal care compositions (e.g., cosmetic compositions), including hair care compositions such as styling agents (e.g., hair sprays, styling mousses, styling gels), shampoos, dyes, conditioners, rinses, and antidandruff preparations. Other personal care compositions include insect repellants, shaving products, hand and body lotions, gels, creams, moisturizers, sunless tanning compositions, cleansers, toners, astringents, fresheners, and masks for the hair and skin, polishes and strengtheners for the nails, underarm deodorants and antiperspirants, bath powders, talcs, bath oils, bubble baths, makeup products such as makeup for the eyes, cheeks, and lips, colognes, perfumes, compositions for cushioning sores, and hair removal compositions.

Examples of specific products that could especially benefit from having present the water-in-oil emulsions of the present invention, include but are not limited to, lipsticks (both solid and liquid at room temperature and which provide glossy or matte finish), eye shadows (both solid and liquid at room temperature and which provide glossy or matte finish), eye liners, mascara, rouge, face powder, foundation (both solid and liquid at room temperature and which provide glossy or matte finish), compositions for masking or camouflaging skin blemishes, sunscreens (organic, inorganic, or combinations thereof), and temporary hair coloring compositions (whole head, streaks and/or highlights).

Accordingly, in addition to the additives listed above, emulsions of the present invention may include other materials to provide therapeutic or protective cosmetic utility. Examples include conditioners, sunscreen agents, insect repellents, vitamins, herbal extracts, antiperspirant or deodorant agents, skin or hair bleaching or coloring agents including sunless tanning agents, depilating agents, antidandruff agents, antiacne agents, astringents, tensors, skin toning agents, or corn, callus, or wart removers. The emulsions also may include materials having decorative or color cosmetic utility, for example, by incorporation of glitter, pigments, dyes, bleaches, perfumes, or fragrances.

Other materials conventionally used in cosmetic compositions, such as preservatives, antioxidants, waxes, film-forming polymers, propellants, buffers, organic or inorganic suspending or thickening agents, plasticizers, herbal extracts, and flavoring agents can also be included in minor amounts of the emulsions of the present invention, preferably in amounts that do not adversely affect the substantivity of the compositions. These materials can be added to the aqueous or oil phase (depending on solubility) prior to emulsification, or added after the emulsions have been prepared and cooled. The latter is preferred when materials with heat sensitivity are used.

Preferred cosmetic preparations of the present invention do not transfer certain ingredients (such as coloring agents) from the surface applied, such as skin or hair, to unintended surfaces, such as clothing or upholstery. Such preferred cosmetic preparations are described as having transfer resistant or transfer proof properties. The preferred water-in-oil emulsions can be prepared by conventional methods, such as slowly adding a heated water phase material to a heated oil phase material and agitating or homogenizing with a high-speed mixer. It is well known to one skilled in the art that a variety of ingredients or combination of ingredients and active agents can be utilized to obtain a cosmetic formulation optimized for a particular utility or market segment. A typical reference source that lists standard cosmetic ingredients is the International Cosmetic Ingredient Dictionary and Handbook, published by The Cosmetic, Toiletry, and Fragrance Association, John A. Wenninger and G. N. McEwen, Jr., Editors, 7th Edition, 1997.

EXAMPLES

The objects, features and advantages of the present invention illustrated in the following examples, which incorporate particular materials and amounts, should not be construed to unduly limit this invention. All materials are commercially available.

GLOSSARY

| | |
|---|---|
| AMPS 2401 | $CH_2$=CH—C(O)—NHC($CH_3$)$_2$$CH_2$$SO_3$H (Lubrizol, Wickliffe, OH) |
| NVP | N-vinyl pyrrolidone (International Specialty Products Technologies, Wayne, NJ) |
| HEMA | 2-hydroxyethyl methacrylate (Sigma-Aldrich Fine Chemicals, St. Louis, MO) |
| IOA | Isooctyl Acrylate (3M Company, St. Paul, MN) |
| SMA | Stearyl Methacrylate (Rocryl 331, Rohm and Hass, Philadelphia, PA) |
| AA | Acrylic Acid (BASF Corporation, Mount Olive, NJ) |
| EAc | Ethyl Acetate (EM Science, Gibbstown, NJ which is a Division of EM Industries, Hawthorne, NY) |
| IPP | Isopropyl Palmitate (Sigma-Aldrich Fine Chemicals) |
| DMF | Dimethyl Formamide (Mallinckrodt Inc., Paris, KY) |
| VAZO 67 | 2,2'-Azobis(2-methylbutanenitrile) (E. I. du Pont de Nemours and Company, Wilmington, DE) |
| E/AA | Ethylene/Acrylic Acid (as AC540 from Allied Signal, Morristown, NJ) |
| DOCH | Dioctyl Cyclohexane (as Cetiol S from Henkel, Hoboken, NJ) |
| DIPS | Diisopropyl sebecate (as Dermol DIPS from Alzo, Sayerville, NJ) |
| PPG(15) | Polypropylene Glycol (15) Stearyl Ether (as Arlamol E from ICI, Wilmington, DE) |
| $MgSO_4 \cdot 7H_2O$ | Magnesium Sulfate Heptahydrate (Sigma-Aldrich Fine Chemicals, Inc.) |
| PVP/I | Polyvinylpyrrolidone/Iodine (BASF, Wyandotte, MI) |

Test Protocols

Emulsion Stability

A 10-milliliter (10-ml) sample of an emulsion formulation was placed in a 15 ml plastic graduated Corning disposable centrifuge tube. The tube was frozen at −20° C. for approximately 2 hours, then thawed to room temperature (23–25° C.) for approximately 2 hours, and centrifuged for 10 minutes at 3000 RPMs using a Labofuge B, model 2650 manufactured by Heraeus Sepatech GMBH, Osterode, West Germany. The freeze/thaw/centrifuge process was repeated a maximum of 3 cycles. A stable formulation had no visible separation at the end of the one, preferably at the end of two and most preferably at the end of three freeze/thaw/centrifuge cycles.

Starting Materials

Polymeric Emulsifier Preparation A: SMA/IOA/AMPS Copolymer

The amounts of each chemical compound given in Table 1a were weighed into a 4-ounce (115-ml) flint glass narrow mouth bottle.

TABLE 1a

Materials used in SMA/IOA/AMPS Copolymer Preparation

| Amount (grams) | Description |
|---|---|
| 4.86 | SMA |
| 4.14 | IOA |
| 1.00 | AMPS 2401 |
| 23.00 | IIP |

TABLE 1a-continued

Materials used in SMA/IOA/AMPS Copolymer Preparation

| Amount (grams) | Description |
|---|---|
| 15.00 | DMF |
| 0.04 | VAZO 67 |

The mixture was purged with nitrogen to remove oxygen and sealed with a TEFLON (Registered Trademark of E.I. du Pont de Nemours and Company) fluoropolymer resin lined metal cap. The bottle was placed in an apparatus for rotating closed containers in a thermostatically controlled water bath at 42 rotations per minute (commercially available as Launder-Ometer from Atlas Electric Devices Co., Chicago, Ill.), which had been preheated to 65° C. for 64 hours. After this time the sample was viscous and cloudy. An additional 17 grams (g) quantity of IPP was added and the DMF was removed by stripping the solvent on a rotary evaporator. The polymeric emulsifier was supplied as a 20 percent by weight solid solutions in IPP and designated polymeric emulsifier A.

Polymeric Emulsifier Preparation B: SMA/IOA/NVP Copolymer

The amounts of each chemical compound given in Table 1b were weighed into a 4-oz (115-ml) flint glass narrow mouth bottle.

TABLE 1b

Materials used in 51/44/5 SMA/IOA/NVP Copolymer Preparation

| Amount (grams) | Description |
|---|---|
| 13.85 | SMA |
| 11.80 | IOA |
| 1.35 | NVP |
| 33.00 | Eac |
| 0.081 | VAZO 67 |

The mixture was purged with nitrogen to remove oxygen and sealed with a TEFLON fluoropolymer resin lined metal cap. The bottle was placed in an apparatus for rotating closed containers in a thermostatically controlled water bath at 42 rotations per minute (commercially available as Launder-Ometer from Atlas Electric Devices Co., Chicago, Ill.), which had been preheated to at 65° C. and maintained at that temperature for 48 hours. After this time the reaction mixture was hazy and had high viscosity. Diisopropyl sebecate (81 g) was added to the reaction mixture and the ethyl acetate reaction solvent was removed on a rotary evaporator yielding a solution of the polymer in DIPS at 25% solids and designated polymeric emulsifier B.

Polymeric Emulsifier Preparation C: SMA/IOA/HEMA Copolymer

The amounts of each chemical compound given in Table 1c were weighed into a 4-oz (115-ml) flint glass narrow mouth bottle.

TABLE 1c

Materials used in 51/44/5
SMA/IOA/HEMA Copolymer Preparation

| Amount (grams) | Description |
|---|---|
| 13.85 | SMA |
| 11.80 | IOA |
| 1.35 | HEMA |
| 33.0 | Eac |
| 0.081 | VAZO 67 |

The copolymer was prepared as described in Emulsion Preparation B. The reaction mixture was clear and had high viscosity. Once again 81 grams of diisopropyl sebecate was added to the reaction mixture and the ethyl acetate reaction solvent was removed on a rotary evaporator yielding a solution of the polymer in DIPS at 25% solids and designated polymeric emulsifier C.

Polymeric Emulsifier Preparation D: SMA/IOA/AA Copolymer

The amounts of each chemical compound given in Table 1d are weighed into a 4-oz (115-ml) flint glass narrow mouth bottle.

TABLE 1d

Materials to use in 50/43/7
SMA/IOA/AA Copolymer Preparation

| Amount (grams) | Description |
|---|---|
| 5.00 | SMA |
| 4.30 | IOA |
| 0.70 | AA |
| 12.20 | Eac |
| 0.035 | VAZO 67 |

The mixture is purged with nitrogen to remove oxygen and is sealed with a TEFLON fluoropolymer resin lined metal cap. The bottle is placed in an apparatus for rotating closed containers in a thermostatically controlled water bath at 42 rotations per minute (commercially available as Launder-Ometer from Atlas Electric Devices Co.) which is preheated to at 60° C. and is maintained at that temperature for 48 hours. The reaction mixture is clear and has high viscosity. Diisopropyl sebecate is added to the reaction mixture and the ethyl acetate reaction solvent is removed on a rotary evaporator yielding a solution of the polymer in DIPS at 25% solids and designated polymeric emulsifier D.

Example 1 and Comparative Examples A and B

The polymeric emulsifiers A, B, and C were used to prepare water-in-oil emulsions with antimicrobial compounds for disinfecting tissue in Example 1 and Comparative Examples A and B respectively. The composition of the water-in-oil emulsions are given in Table 1e.

TABLE 1e

Composition of Water-in-oil Emulsions

| | Compound | Weight (grams) | Weight (percent) |
|---|---|---|---|
| Oil Phase | | | |
| Ex. 1 | 20 percent (49/41/10 SMA/IOA/AMPS) Copolymer/80 percent IPP (Polymeric Emulsifier A) | 12.0 | 11.4 |
| Comp. Ex. A | 25 percent (51/44/5 SMA/IOA/NVP) Copolymer/75 percent DIPS (Polymeric Emulsifier B) | | |
| Comp. Ex. B | 25 percent (51/44/5 SMA/IOA/HEMA) Copolymer/75 percent DIPS (Polymeric Emulsifier C) | | |
| | E/AA | 2.5 | 2.4 |
| | DOCH | 5.0 | 4.7 |
| | DIPS | 20.0 | 19.0 |
| | PPG (15) SE | 6.0 | 5.7 |
| Water Phase | | | |
| | Water | 49.5 | 47.0 |
| | MgSO$_4$.7H$_2$O | 0.5 | 0.47 |
| | PVP/I | 10.0 | 9.5 |

The process for making the water-in-oil emulsion consisted of the following steps:

1) The pH of the water phase was measured and adjusted to 3–4 using sodium hydroxide.
2) The oil phase was heated at 100° C. for 2 hours, and the water phase at 100° C. for 15 minutes (min) in an oven.
3) Then the water phase (100° C.) was added to oil phase (100° C.) over about 1 to 2 minutes with a Silverson homogenizer on high speed with a 1-inch (2.54-cm) diameter high shear head followed by continuously mixing for another 1 min at high rate.
4) Next the emulsion was placed in a steam jacket and mixed with an overhead air motor and T shaped impeller at a temperature of approximately 80° C. for 15 minutes with vigorous overhead stirring.
5) Finally, the emulsion was cooled slowly to 40° C. with mixing in the same apparatus (Steam turned off).

Example 1 specifically is a water-in-oil emulsion containing povidone/iodine USP wherein the water phase has a pH of 3–4. The water-in-oil emulsion made with the 49/41/10 SMA/IOA/AMPS polymeric emulsifier was stable through 5 freeze/thaw/centrifuge cycles. The 49/41/10 SMA/IOA/AMPS polymer produced stable emulsions showing that the sulfonated monomers are effective emulsifiers even at low pH of less than 4. The polymeric emulsifiers used in Comparative Examples A and B did not produce an emulsion. Complete results are summarized in the Table 1f.

TABLE 1f

Water Phase pH and Water-in-oil
Emulsion Viscosity and Stability

| Ex. | pH | Viscosity | Stability |
|---|---|---|---|
| 1 | 3.8 | Light | Uniform |
| Comp. A | 3.9 | Very light | Separated immediately |

TABLE 1f-continued

Water Phase pH and Water-in-oil Emulsion Viscosity and Stability

| Ex. | pH | Viscosity | Stability |
|---|---|---|---|
| Comp. B | 3.9 | Very light | Separated immediately |

Example 2

Example 2 is also a water-in-oil emulsion containing povidone/iodine USP wherein the water phase has a pH of 3–4. The composition of the water-in-oil emulsion is given in Table 2a.

TABLE 2a

Composition of Water-in-oil Emulsion

| | Compound | Weight (grams) | Weight (percent) |
|---|---|---|---|
| Oil Phase | | | |
| Example 2 | 20 percent AMPS Copolymer/ 80 percent IPP | 15.0 | 13.8 |
| | E/AA | 2.5 | 2.3 |
| | DOCH | 5.0 | 4.6 |
| | DIPS | 20.0 | 18.0 |
| | PPG (15) SE | 6.0 | 5.5 |
| Water Phase | | | |
| | Water | 49.5 | 45.6 |
| | MgSO$_4$.7H$_2$O | 0.5 | 0.46 |
| | PVP/I | 10.0 | 9.2 |

The process for making the water-in-oil emulsion was the same as in Example 1.

The water-in-oil emulsion made with the SMA/IOA/AMPS polymeric emulsifier was stable through 1 freeze/thaw/centrifuge cycle. Complete results are summarized in the Table 2b.

TABLE 2b

Water phase pH and Water-in-oil Emulsion Viscosity, Stability and Appearance

| Ex. | pH | Viscosity | Stability | Appearance |
|---|---|---|---|---|
| 2 | 3 | Thick | Uniform for 1 freeze/thaw/ centrifuge cycle | Uniform and darker brown |

Comparative Example C

The polymeric emulsifier D was used to prepare a water-in-oil emulsion with antimicrobial compounds for disinfecting tissue in Comparative Example C. The composition of the water-in-oil emulsion is given in Table 3a.

TABLE 3a

Composition of Water-in-oil Emulsion without PVP/I$_2$

| | Compound | Weight (grams) | Weight (percent) |
|---|---|---|---|
| Oil Phase | | | |
| Comp. Ex. C | 25 percent (50/43/7 SMA/IOA/AA) Copolymer/75 percent DIPS (Polymeric Emulsifier D) | 8 | 8.9 |
| | E/AA | 2.5 | 2.8 |
| | DOCH | 5.0 | 5.6 |
| | DIPS | 20.0 | 22.2 |
| | PPG (15) SE | 6.0 | 6.7 |
| Water Phase | | | |
| | Deionized Water | 48 | 53.3 |
| | MgSO$_4$.7H$_2$O | 0.48 | 0.53 |

Modifications were made to the water phase and are shown in Table 3b.

TABLE 3b

Modification to Water Phase of Table 3a made by adjusting pH.

| Run No. | Formulation of Water Phase | pH |
|---|---|---|
| 1 | As described in Table 3a | neutral |
| 2 | Formulation of Table 3a plus 5 weight percent PVP/I$_2$ | 3 |
| 3 | Formulation of Table 3a without MgSO$_4$ plus 5 weight percent PVP/I$_2$ | 3 |
| 4 | Formulation of Table 3a plus NaOH and 5 weight percent PVP/I$_2$[1] | 5 |
| 5 | Formulation of Table 3a plus NaOH and 5 weight percent PVP/I$_2$[1] | 6.6 |

[1]NaOH added to adjust pH

The process for making the water-in-oil emulsion consisted of the following steps:

1) The pH of the water phase was measured and adjusted using sodium hydroxide.
2) The oil and water phases were heated separately to 100° C.
3) Then the oil phase (100° C.) was added to water phase (100° C.) over about 1 to 2 minutes with a Silverson homogenizer on high speed with a 1-inch (2.54-cm) diameter high shear head followed by continuously mixing for another 1 min at high rate. The contents were insulated to maintain temperature
4) Next the emulsion was mixed vigorously with an overhead 45 degree pitched 3 blade impeller for 15 minutes.
5) The composition was sealed and placed on a roller to cool.

After 24 hours the runs 1–5 were subjected to the stability test described in the Test Protocols. Table 3c shows the results of the stability test and a description of the viscosity of the emulsions.

TABLE 3c

Viscosity and Stability of Runs 1–5 of Comparison Example C.

| Run No. | Viscosity | Freeze(F)/Thaw(T)/Centrifuge(CF) Cycles (Description and Approximate Amount of seperation in milliliters) | | | | | |
|---|---|---|---|---|---|---|---|
| | | 1 F/T | 1 CF | 2 F/T | 2 CF | 3F/T | 3 CF |
| 1 | Medium | 0 | 0 | 0 | 0 | 0 | 0 |
| 2 | Medium | Dark dots[1] | 0.1 | Dark dots; 0.2 | 0.5 | Dark dots; 0.5 | 1.2 |
| 3 | Medium | Dark dots | 0.5 | Dark dots; 1.0 | 1.5 | Dark dots; 1.5 | 2.0 |
| 4 | Medium | Dark dots | 0.2 | Dark dots; 0.5 | 0.6 | 0.6 | 1.0 |
| 5 | Medium | Dark dots | 0.1 | Dark dots; 0.2 | 0.3 | 0.3 | 0.5 |

[1]These dots appeared to perhaps be an iodine containing phase.

The results indicate that higher pH yields more stable emulsions, however, even the pH 6.6 (Run 5) emulsion was slightly unstable. Magnesium sulfate adds to the emulsion stability.

Example 3

A series of oils were applied to forearms of various individuals, which were recently washed with white soap and completely dried in a thin film, by applying a drop and rubbing it around with a finger. A single drop (about 20 milligrams (mg)) covered an area approximately 20–25 cm². Immediately after spreading the emollients on the skin a piece of adhesive-coated incise drape material commercially available under the trade designation IOBAN II from 3M Co., St. Paul, Minn., was placed over the emollient area. The adhesion was evaluated qualitatively after 1 minute and 5 minute intervals in contact with the emollient coated skin. The following ratings were used to evaluate adhesion:

6=better than adhesion to dry skin.
5=equal to Ioban™ adhesion to dry skin at a near-by site
4=slightly less than adhesion to dry skin
3=less than adhesion to dry skin
2=much less than adhesion to dry skin
1=very poor—almost falls off

TABLE 4

Results of IOBAN II Adhesion to Emollient Coated Skin

| Emollient | After 5 Minutes | After 1 Minute | Chemical Name |
|---|---|---|---|
| Baseline (no oil) | 5 | 5 | No oil |
| DOWANOL PnB (Sigma-Aldrich Fine Chemicals) | 6 | 4 | Propylene glycol monobutyl ether |
| DERMOL 489 (Alzo, Inc.) | 6 | 5 | Diethylene glycol dioctanoate/disolvate |
| DERMOL 489 (Alzo, Inc.) ("thicker")[1] | 3 | 1 | Diethylene glycol dioctanoate/disolvate |
| DERMOL 109 (Alzo, Inc.) | 5 | 5 | Isodecylisononanoate |
| DMI (Unichema, Wilmington, DE) | 4 | 3 | Dimethylisosorbide |
| DMI (Unichema) ("thicker")[1] | 4 | 3 | Dimethylisosorbide |
| ARLASOLV DPM (Lyondell, Houston, TX) | 4 | 5 | PPG2 Methyl ether |
| CRODAMOL GTCC (Croda, Parsippany, NJ) | 4 | 6 | Capric triglyceride |
| DERMOL DIA (Alzo, Inc.) | 4 | 5 | Dioctyl adipate |
| SPAN 80 (ICI) | 3.5 | 5 | Sorbitan monooleate |
| SPAN 85 (ICI) | 3.5 | 5 | Sorbitan trioleate |
| Propylene glycol (Sigma-Aldrich Fine Chemicals) | 3 | 4 | Propylene glycol |
| Propylene glycol (Sigma-Aldrich Fine Chemicals) ("thicker")[1] | 2 | 3 | Propylene glycol |
| 1,4-Butane diol (Sigma-Aldrich Fine Chemicals) | 3 | 5 | 1,4-Butane diol |
| TRIACETIN (Eastman, Kingsport, TN) | 2 | 1 | Glycerol triacetate |
| TWEEN 80 (HLB15) (ICI) | 1 | 1 | Polyoxyethylene 20 monooleate |
| DERMOL G-7DI (Alzo, Inc.) | 1 | 1 | Glycereth 7 Diisononanoate |

[1]("thicker") Emollients were applied at approximately twice the level.

The results indicate that thin films allow adhesion much more than thicker films. Furthermore, the more hydrophobic emollients exhibit much better adhesion. For example, a more hydrophobic ether (DOWANOL PnB) adheres better than a less hydrophobic ether (ARLASOLV DPM), SPAN 80 adheres much better than TWEEN 80, and ester emollients such as DERMOL 489, DERMOL 109, CRODAMOL GTCC adhere much better than TRIACETIN. The polar glycols did not adhere well. This indicates that the oil phase and water phase ingredients can dramatically effect the adhesion of pressure sensitive adhesives to the emulsions of this invention.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A stable water-in-oil emulsion comprising: a vinyl polymer comprising anionic group-containing side chains and alkyl-Y-containing side chains, wherein Y is O or NR, wherein R is hydrogen or methyl, and wherein the alkyl group of the alkyl-Y-containing side chain has at least 4 carbon atoms on average in a cyclic, branched-, or straight-chain configuration and optionally includes one or more heteroatoms; an oil phase; and a water phase; wherein the vinyl polymer is insoluble or sparingly soluble in the water phase and is derived from at least three different monomers; wherein at least one monomer has a pKa of less than 4 and has the formula:

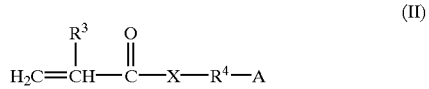

(II)

wherein:

X is O or $NR^5$;

$R^3$ and $R^5$ are each independently hydrogen or methyl;

$R^\alpha$ is a linear, branched, or cyclic alkylene, arylene, or aralkylene group optionally including one or more heteroatoms;

A is $(SO_3)_xM$, $(SO_4)_xM$, $(PO_3)_xM$, $(PO_4)_xM$;

x is 1 or 2; and

M is selected from the group consisting of H, Na, K, Li, Ca, Mg, Zn, a protonated primary amine, a protonated secondary amine, a protonated tertiary amine, a quaternary amine, and combinations thereof; and further wherein at least two monomers have the formula:

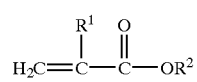 (I)

wherein;

$R^1$ is hydrogen or methyl; and in one monomer, $R^2$ is a linear, branched, or cyclic alkyl group having 4 to 14 carbon atoms on average, optionally including one or more heteroatoms; and in the one monomer, $R^2$ is a linear, branched, or cyclic alkyl group having 15 to 22 carbon atoms on average, optionally including one or more heteroatoms.

2. The water-in-oil emulsion of claim 1 wherein the anionic groups and alkyl-Y groups are in different side chains.

3. The water-in-oil emulsion of claim 1 which is substantive.

4. The water-in-oil emulsion of claim 1 wherein the oil phase comprises one or more oils present in a total amount of at least about 20 wt-%, based on the total weight of the emulsion.

5. The water-in-oil emulsion of claim 1 wherein M is selected from the group consisting of Na, K, Li, Ca, Mg, Zn, a protonated primary amine, a protonated secondary amine, a protonated tertiary amine, a quaternary amine, and combinations thereof.

6. The water-in-oil emulsion of claim 1 wherein M is H.

7. The water-in-oil emulsion of claim 1 wherein the vinyl polymer is the reaction product of:

about 60 wt-% to about 95 wt-% of at least one monomer of Formula I;

about 5 wt-% to about 40 wt-% of at least one monomer of Formula II, or salt thereof; and at least one different monomer.

8. A composition comprising the water-in-oil emulsion of claim 1 and further comprising at least one bioactive agent.

9. The composition of claim 8 wherein the bioactive agent is an antimicrobial.

10. The composition of claim 9 wherein the antimicrobial is an iodophor.

11. The composition of claim 10 wherein the iodophor is povidone-iodine.

12. The water-in-oil emulsion of claim 1 wherein a pressure sensitive adhesive article applied over the emulsion on skin adheres at a level of at least about 50% of the level of adhesion of the pressure sensitive adhesive tape applied directly to the skin.

13. The water-in-oil emulsion of claim 1 wherein the vinyl polymer has an acid equivalent weight of about 1000 to about 6500 grams of polymer per equivalent of low pKa acid.

14. The water-in-oil emulsion of claim 1 comprising at least about 0.25 wt-% of the vinyl polymer, based on the total weight of the emulsion.

15. The water-in-oil emulsion of claim 1 comprising no more than about 10 wt-% of the vinyl polymer, based on the total weight of the emulsion.

16. A composition comprising the water-in-oil emulsion of claim 1 and further comprising one or more additives selected from the group consisting of humectants, surfactants, conditioners, sunscreen agents, insect repellents, vitamins, herbal extracts, antiperspirant or deodorant agents, skin bleaching agents, skin coloring agents, hair bleaching agents, hair coloring agents, depilating agents, antidandruff agents, antiacne agents, astringents, tensors, skin toning agents, glitter, pigments, dyes, bleaches, perfumes, fragrances, preservatives, antioxidants, waxes, film-forming polymers, propellants, buffers, organic suspending agents, inorganic suspending agents, organic thickening agents, inorganic thickening agents, plasticizers, herbal extracts, flavoring agents, corn, callus, or wart removers, and combinations thereof.

17. A stable moisturizing composition comprising a water-in-oil emulsion comprising: a vinyl polymer comprising anionic group-containing side chains and alkyl-Y-containing side chains, wherein Y is O or NR, wherein R is hydrogen or methyl, and wherein the alkyl group of the alkyl-Y-containing side chain has at least 4 carbon atoms on average in a cyclic, branched-, or straight-chain configuration, with the proviso that the alkyl group of the alkyl-Y-containing side chain does not comprise heteroatoms; an oil phase; and a water phase; wherein the vinyl polymer is derived from at least three different monomers; wherein at least one monomer has a pKa of less than 4 and has the formula:

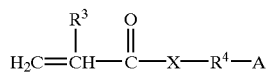 (II)

wherein:

X is O or $NR^5$;

$R^3$ and $R^5$ are each independently hydrogen or methyl;

$R^4$ is a linear, branched, or cyclic alkylene, arylene, or aralkylene group optionally including one or more heteroatoms;

A is $(SO_3)_xM$, $(SO_4)_xM$, $(PO_3)_xM$, $(PO_4)_xM$;

x is 1 or 2; and

M is selected from the group consisting of H, Na, K, Li, Ca, Mg, Zn, a protonated primary amine, a protonated secondary amine, a protonated tertiary amine, a quaternary amine, and combinations thereof; and further wherein at least two monomers have the formula:

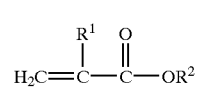 (I)

wherein:

$R^1$ is hydrogen or methyl; and in one monomer, $R^2$ is a linear, branched, or cyclic alkyl group having 4 to 14 carbon atoms on average, optionally including one or more heteroatoms;

and in the other monomer, $R^2$ is a linear, branched, or cyclic alkyl group having 15 to 22 carbon atoms on average, optionally including one or more heteroatoms.

18. A stable mammalian tissue antiseptic composition comprising an antimicrobial agent and a water-in-oil emulsion comprising: a vinyl polymer comprising anionic group-containing side chains and alkyl-Y-containing side chains, wherein Y is O or NR, wherein R is hydrogen or methyl, and wherein the alkyl group or the alkyl-Y-containing side chain has at least 4 carbon atoms on average in a cyclic, branched-, or straight-chain configuration, with the proviso that the alkyl group of the alkyl-Y-containing side chain does not comprise heteroatoms; an oil phase; and a water phase; wherein the vinyl polymer is derived from at least three different monomers;

wherein at least one monomer has a pKa of less than 4 and has the formula:

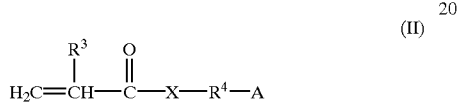

(II)

wherein:

X is O or $NR^5$;

$R^3$ and $R^5$ are each independently hydrogen or methyl;

$R\alpha$ is a linear, branched, or cyclic alkylene, arylene, or aralkylene group optionally including one or more heteroatoms;

A is $(SO_3)_xM$, $(SO_4)_xM$, $(PO_3)_xM$, $(PO_4)_xM$;

x is 1 or 2; and

M is selected from the group consisting of H, Na, K, Li, Ca, Mg, Zn, a protonated primary amine, a protonated secondary amine, a protonated tertiary amine, a quaternary amine, and combinations thereof; and further wherein at least two monomers have the formula:

(I)

wherein:

$R^1$ is hydrogen or methyl; and in one monomer, $R^2$ is a linear, branched, or cyclic alkyl group having 4 to 14 carbon atoms on average, optionally including one or more heteroatoms;

and in the other monomer, $R^2$ is a linear, branched, or cyclic alkyl group having 15 to 22 carbon atoms on average, optionally including one or more heteroatoms.

19. A stable personal care composition comprising a water-in-oil emulsion comprising a vinyl polymer comprising anionic group-containing side chains and alkyl-Y-containing side chains, wherein Y is O or NR, wherein R is hydrogen or methyl, and wherein the alkyl group of the alkyl-Y-containing side chain has at least 4 carbon atoms on average in a cyclic, branched-, or straight-chain configuration, with the proviso that the alkyl group of the alkyl-Y-containing side chain does not comprise heteroatoms; an oil phase; and a water phase; wherein the vinyl polymer is derived from at least three different monomers; wherein at least one monomer has a pKa of less than 4 and has the formula:

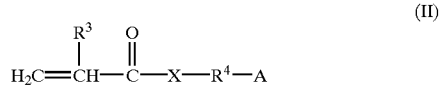

(II)

wherein:

X is O or $NR^5$;

$R^3$ and $R^5$ are each independently hydrogen or methyl;

$R\alpha$ is a linear, branched, or cyclic alkylene, arylene, or aralkylene group optionally including one or more heteroatoms;

A is $(SO_3)_xM$, $(SO_4)_xM$, $(PO_3)_xM$, $(PO_4)_xM$;

x is 1 or 2; and

M is selected from the group consisting of H, Na, K, Li, Ca, Mg, Zn, a protonated primary amine, a protonated secondary amine, a protonated tertiary amine, a quaternary amine, and combinations thereof; and further wherein at least two monomers have the formula:

(I)

wherein:

$R^1$ is hydrogen or methyl; and in one monomer, $R^2$ is a linear, branched, or cyclic alkyl ground having 4 to 14 carbon atoms on average, optionally including one or more heteroatoms;

and in the other monomer, $R^2$ is a linear, branched, or cyclic alkyl group having 15 to 22 carbon atoms on average, optionally including one or more heteroatoms.

20. A stable drug delivery composition comprising a pharmaceutical agent and a water-in-oil emulsion comprising: a vinyl polymer comprising anionic group-containing side chains and alkyl-Y-containing side chains, wherein Y is O or NR, wherein R is hydrogen or methyl, and wherein the alkyl group of the alkyl-Y-containing side chain has at least 4 carbon atoms on average in a cyclic, branched-, or straight-chain configuration, with the proviso that the alkyl group of the alkyl-Y-containing side chain does not comprise heteroatoms; an oil phase; and a water phase; wherein the vinyl polymer is derived from at least three different monomers;

wherein at least one monomer has a pKa of less than 4 and has the formula:

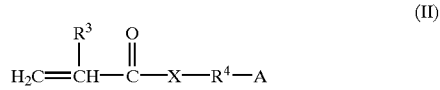

(II)

wherein:

X is O or $NR^5$;

$R^3$ and $R^5$ are each independently hydrogen or methyl;

$R\alpha$ is a linear, branched, or cyclic alkylene, arylene, or aralkylene group optionally including one or more heteroatoms;

A is $(SO_3)_xM$, $(SO_4)_xM$, $(PO_3)_xM$, $(PO_4)_xM$;

x is 1 or 2; and

M is selected from the group consisting of H, Na, K, Li, Ca, Mg, Zn, a protonated primary amine, a protonated secondary amine, a protonated tertiary amine, a quaternary amine, and combinations thereof; and further wherein at least two monomers have the formula:

 (I)

wherein:

$R^1$ is hydrogen or methyl; and in one monomer, $R^2$ is a linear, branched, or cyclic alkyl ground having 4 to 14 carbon atoms on average, optionally including one or more heteroatoms;

and in the other monomer, $R^2$ is a linear, branched, or cyclic alkyl group having 15 to 22 carbon atoms on average, optionally including one or more heteroatoms.

* * * * *

UNITED STATES PATENT AND TRADEMARK OFFICE
CERTIFICATE OF CORRECTION

PATENT NO. : 6,951,642 B2  
APPLICATION NO. : 09/967578  
DATED : October 4, 2005  
INVENTOR(S) : Matthew T. Scholz It is certified that error appears in the above-identified patent and that said Letters Patent is hereby corrected as shown below:

Title Page  
Item [56], References Cited, OTHER PUBLICATIONS, line 7, delete "Cádenas" and insert -- Cárdenas --, therefore.  
Item [56], References Cited, OTHER PUBLICATIONS, line 12, delete "Cádenas" and insert -- Cárdenas --, therefore.

Column 2  
Line 26, after "group of" insert -- the --.

Column 25  
Line 4, delete "R∞" and insert -- $R^4$ --, therefore.  
Line 20, after "wherein" delete ";" and insert -- : --, therefore.  
Line 26, delete "one" and insert -- other --, therefore.

Column 27  
Line 10, delete "or" and insert -- of --, therefore.  
Line 30, delete "R∞" and insert -- $R^4$ --, therefore.

Column 28  
Line 13, delete "R∞" and insert -- $R^4$ --, therefore.  
Line 35, delete "ground" and insert -- group --, therefore.  
Line 65, delete "R∞" and insert -- $R^4$ --, therefore.

Column 30  
Line 6, delete "ground" and insert -- group --, therefore.

Signed and Sealed this

Thirty-first Day of July, 2007

JON W. DUDAS  
*Director of the United States Patent and Trademark Office*